United States Patent [19]
Dorigatti et al.

[11] Patent Number: 5,658,582
[45] Date of Patent: Aug. 19, 1997

[54] MULTILAYER NONWOVEN TISSUE CONTAINING A SURFACE LAYER COMPRISING AT LEAST ONE HYALURONIC ACID ESTER

[75] Inventors: Franco Dorigatti, Trento; Lanfranco Callegaro, Padua, both of Italy

[73] Assignee: Fidia Advanced Biopolymers S.r.l., Brindisi, Italy

[21] Appl. No.: 505,325

[22] PCT Filed: Feb. 11, 1994

[86] PCT No.: PCT/EP94/00397

§ 371 Date: Oct. 10, 1995

§ 102(e) Date: Oct. 10, 1995

[87] PCT Pub. No.: WO94/17837

PCT Pub. Date: Aug. 18, 1994

[30] Foreign Application Priority Data

Feb. 12, 1993 [IT] Italy .................. PD93A0024

[51] Int. Cl.⁶ .................. A01N 25/34; A61L 15/16; B32B 5/22; B32B 17/02
[52] U.S. Cl. .................. 424/402; 424/404; 424/444; 428/113; 602/45
[58] Field of Search .................. 424/402, 404, 424/444; 428/113, 224, 280, 288, 289; 602/45

[56] References Cited

U.S. PATENT DOCUMENTS

| | | |
|---|---|---|
| 4,851,521 | 7/1989 | della Valle et al. . |
| 4,965,353 | 10/1990 | Della Valle et al. .................. 536/55.1 |
| 5,202,431 | 4/1993 | della Valle et al. . |
| 5,264,422 | 11/1993 | della Valle et al. . |
| 5,520,915 | 5/1996 | Dorigatti .................. 424/402 |

FOREIGN PATENT DOCUMENTS

| | | |
|---|---|---|
| A-67717 | 6/1991 | Australia . |
| B-16601 | 10/1995 | Australia . |
| 0177477 | 4/1986 | European Pat. Off. . |
| 216453 | 6/1987 | European Pat. Off. . |
| 462426 | 5/1991 | European Pat. Off. . |
| 2617502 | 1/1989 | France . |
| 93 11803 | 6/1993 | WIPO . |
| 94 01468 | 1/1994 | WIPO . |
| 09122 | 4/1994 | WIPO . |

OTHER PUBLICATIONS

Yu, et al., BA Biochimica et Biohysica Acta, Elsevier Science, "a–1,4–*Glucan lyase, a new class of starch/glycogen degrading enzyme*," 1156:313–320, (1993).

Baute, et al., Bull. Soc. Pharm. Bordeaux, "Bioconversions Fongiques Produisant, A Partr De Sucres, Des Composes Pyrontiques Inhabituels a Activite Antibiotique," 128:9–18 (1989).

Shukun Yu and Marianne Pedersen, Planta, "a–1,4, *Glucan lyase, a new class of starch/glycogen–degrading enzyme*," 191:137–143 (1993).

Plant Physiology, Biochemistry and Biophysics, Bio. Abstr. 57: AB–926, No. 52735, referencing Baute, et al., Phytochemistry, 27:3401–3404 (1988).

Baute, et al., Phytochemistry, "*Fungal Enzymic Activity Degrading 1,4-a-D-Glucans to 1,5,-D-Anhydrofructose,*" 27:3401–3403 (1988).

*Primary Examiner*—Thurman K. Page
*Assistant Examiner*—Kathryne E. Shelborne
*Attorney, Agent, or Firm*—Birch, Stewart, Kolasch & Birch, LLP

[57] ABSTRACT

Provided is a multilayered of nonwoven material comprising a surface layer which comes into contact with the skin, and one or more other layers which do not come into contact with the skin, wherein said surface layer which comes into contact with the skin is a member selected from the group consisting of a surface layer comprising at least one hyaluronic acid ester, a surface layer comprising a mixture of said at least one hyaluronic acid ester and at least one natural polymer, semisynthetic polymer, or synthetic polymer, and a surface layer comprising a natural, synthetic, or semisynthetic biocompatible perforated membrane compatible with cell growth on its surface. This material can be employed in a wide variety of medical and sanitary applications, including surgery and as a non-adhesive covering material.

26 Claims, No Drawings

MULTILAYER NONWOVEN TISSUE CONTAINING A SURFACE LAYER COMPRISING AT LEAST ONE HYALURONIC ACID ESTER

BACKGROUND OF THE INVENTION

1. Field of the Invention

The present invention relates to a new material, i.e., a multilayer nonwoven tissue, wherein one of the layers comprises a hyaluronic acid derivative.

2. Description of Related Art

Studies aimed at obtaining biomaterials composed of hyaluronic acid esters used as such or in mixtures with other polymers, which provide good skin coverage, have led to the creation of various types of products. Tissues such as the gauzes and films described in U.S. Pat. Nos. 4,851,521 and 4,965,353 have been proposed. Limitations on the use of such products as skin coverings are due to their degree of rigidity, which may vary according to how they are made, and to their poor absorption of fluids, such as those exuding from wounds during tissue repair. By using nonwoven tissue production techniques, it is possible to obtain products which combine flexibility with the capacity to strongly absorb fluids. These characteristics are described in various patents, such as U.S. Pat. No. 5,041,104.

Limitations on the use of products composed of hyaluronic acid derivatives and/or their mixtures, obtained using currently known techniques, can for the most part be attributed to:

(1) the poor mechanical characteristics of the material when wet, due to its tendency to form a gel when it comes into contact with aqueous fluids such as physiological fluids;

(2) the excessive use of expensive materials such as hyaluronic acid derivatives or mixtures thereof with other biocompatible and bioabsorbable polymers, resulting in a high cost of the finished product, despite the fact that the polymer need only be present in the layer directly in contact with the application site; and (3) excessively high vapour transmission values.

These drawbacks are particularly significant in cases where poor exudate production is present.

SUMMARY OF THE INVENTION

Accordingly, an object of the present invention is to provide a multilayer nonwoven material, comprising a surface layer which comes into contact with the skin, and one or more other layers which do not come into contact with the skin, wherein said surface layer which comes into contact with the skin is a member selected from the group consisting of a surface layer comprising at least one derivative of hyaluronic acid, a surface layer comprising a mixture of said at least one derivative of hyaluronic acid and at least one natural polymer, semisynthetic polymer, or synthetic polymer, and a surface layer comprising a natural, synthetic, or semisynthetic biocompatible perforated membrane compatible with cell growth on its surface. In a preferred embodiment, the layer which contacts the skin comprises a hyaluronic acid derivative, i.e., a compound containing a hyaluronic acid moiety, especially a hyaluronic acid ester or mixtures thereof.

Such products possess good mechanical and fluid absorption characteristics, are flexible and soft, reasonably priced, and can be varied with respect to their permeability to water vapours.

Another object of the present invention is to provide a multilayer nonwoven material, wherein said one or more other layers which do not come into contact with the skin comprise a natural, synthetic, or semisynthetic material which acts as a reinforcement and/or a fluid absorption system for said multilayer nonwoven material, thus reducing the quantity of biocompatible and bioabsorbable polymers to a minimum, concentrating their action in the area where it is needed.

A further object of the present invention is to provide a multilayer nonwoven material as above, wherein said surface layer which comes into contact with the skin and said one or more other layers which do not come into contact with the skin are fixed together by at least one member selected form the group consisting of a coagulating chemical agent, an adhesive agent, and mechanical stitches.

Such multilayer nonwoven materials can be used, for example, as non-adhesive sanitary or surgical articles in surgery, in dermatology such as in treating skin pathologies, in odontostomatology, in orthopaedics, in neurosurgery, and in treating the ear or nose.

Further scope of the applicability of the present invention will become apparent from the detailed description provided below. However, it should be understood that the detailed description and specific examples, while indicating preferred embodiments of the present invention, are given by way of illustration only, since various changes and modifications within the spirit and scope of the present invention will become apparent to those skilled in the art from this detailed description.

DETAILED DESCRIPTION OF THE INVENTION

The following detailed description of the invention is provided to aid those skilled in the art in practicing the present invention. However, the following detailed description should not be construed to unduly limit the present invention, as modifications and variations in the embodiments discussed herein may be made by those of ordinary skill in the art without departing form the spirit or scope of the present inventive discovery.

The contents of each of the references cited herein are herein incorporated by reference in their entirety.

The foregoing and other objects are achieved by multilayer nonwoven tissues according to the present invention, with a basis weight of between 20 g/mq and 500 g/mq, a thickness of 0.5 mm to 20 mm, a minimum of 2 to 4 layers, a water absorption percentage compared to their weight of between 60% and 150%, and a water vapour permeability of between 100 and 4500 g/mq in 24 hrs.

The multilayer nonwoven tissue can be described as a material comprising several layers, fixed together by coagulating chemical agents and/or adhesive agents or by mechanical stitching methods. Each layer comprises fibers having a diameter varying between 8 and 60 micrometers and a length of between 5 mm and 100 mm, joined together with coagulating chemical agents or adhesive agents, or by means of mechanical stitches.

The layer which is to come into contact with the skin is comprises of esters of hyaluronic acid such as those described in EPA 0 216 453 and U.S. Pat. Nos. 4,851,521, 4,965,353, and 5,202,431, used either singly or in mixtures in varying percentages. Moreover, this layer can also comprise mixtures of fibers of hyaluronic acid esters with fibers obtained ffrom natural polymers such as collagen or collagen and glycosaminoglycan coprecipitates, cellulose, polysacchardies in the form of gels such as chitin, chitosan pectin, or pectic acid, agar, agarose, xanthan gum, gellan, alginic acid, various alginates, alginic acid esters, polymannan or polyglycan, starches, natural gums, or fibers obtained from semisynthetic derivatives of natural polymers such as collagen cross-linked with cross-linking agents such as aldehydes or precursors of the same, dicarboxylic acids or halogenides of the same, diamines, derivatives of cellulose, alginic acid, starch, hyaluronic acid, chitin, chitosan, gellan, xanthan, pectin, pectic acids, polyglycan, polymannan, agar, agarose, natural gums, glycosaminoglycan, or with fibers obtained from synthetic polymers such as polylactic acid, polyglycolic acid or copolymers of the same or their derivatives, polydioxane, polyphosphazene, polysulfone, and polyurethane.

As employed herein, the term "derivative" refers to a compound containing the indicated moiety. For example, the term "cellulose derivative" denotes a compound containing a cellulose moiety.

The upper layers, which have the function of reinforcing the products and/or absorbing fluids and modulating the permeability to water vapours, may be in the form of nonwoven tissues or loom-woven structures. They may be constructed of natural fibers such as cotton, regenerated fibers such as viscose rayon, or fibers of synthetic polymers such as polyesters, polyamides, polyalkylenes, or mixtures thereof. Moreover, the layers can be composed of flexible foams, like polyurethane, or synthetic, elastomeric-type membranes such as elastomeric silicone or elastomeric polyurethane.

The various layers are fixed together by processes typical of nonwoven tissue techniques. These include, for example, mechanical stitching processes or chemical processes employing coagulating or adhesive agents, suitable for consolidating layers of fibers or for joining layers of various kinds, as described in *Nonwoven Technologies for Sanitary Absorbent Products*, pages 185–190. An exemplary adhesive agent is an acrylic ester binder, Acronal DS 2331 X.

The present invention therefore relates to a new class of product, multilayer nonwoven tissues, for use in the medical/pharmaceutical field to cover the skin and in surgery. The surface which comes into contact with the skin is composed of at least one hyaluronic acid ester used as such or in admixture with other natural or synthetic polymers; other layers of synthetic or semisynthetic materials act as reinforcements of the material and/or fluid absorption systems.

The surface layer which comes into contact with the skin can also be comprised of a natural, synthetic, or semisynthetic biocompatible perforated membrane compatible with cell growth on its surface. Examples of such natural and semisynthetic biocompatible perforated membranes are described in EP Application 0 462 426. Natural materials useful in such membranes include collagen or coprecipitates of collagen and glycosaminoglycans, cellulose, gelled polysacharides such as chitin, chitosan, pectins, pectic acids, agar, agarose, xanthan gum, gellan, alginic acid, alginates, polymannans, polyglucans, starches, or natural rubbers, either alone or in mixture with each other or with polymers of synthetic or semisynthetic origin, in the presence of suitable precipitating or gelling agents such as metal slats, polycations, or polyanions. Examples of synthetic biocompatible perforated membranes useful in the present multilayer nonwoven tissue include polylactic acid, polyglycolic acid, copolymers thereof or their derivatives, polydioxanones, polyphosphazenes, polysulfones, polyurethanes, semisynthetic derivatives of natural polymers such as collagen crosslinked with crosslinking agents such as dialdehydes or their precursors, dicarboxylic acids or halides thereof, diamines, or derivatives of cellulose, alginic acid, starch, chitin, chitosan, gellan, xanthan gum, pectins, pectic acids, polyglucans, polymannans, agar, agarose, natural rubbers, or glycosaminoglycans. Such synthetic membranes can also comprise non-biodegradable synthetic polymers such as silicone, silane, or siloxane rubbers, fluoropolymers such as polyfluoroethylene, polyfluoropropylene, polyfluoroethers, polystyrene, vinyl polychloride, polyacrylate or derivatives thereof, polyhydroxyacrylate, polyhydroxymethacrylate, carboxyvinyl polymers and their derivatives, maleic anhydride polymers and their derivatives, polyvinylchloride, polyvinylalcohol and its derivatives, polyethylene, and polypropylene.

The nonwoven tissues of the present invention can also be impregnated with solutions of antibiotics, antiseptics, antimicotics, polypeptides, proteins, or any other type of pharmaceutically active compounds.

The characteristics of the new materials of the present invention make them especially valuable for use in the field of surgery, such as in ontological and otoneurological microsurgery, functional, post-trauma and endoscopic rhinosinusal microsurgery, plastic and reconstructive surgery, and any other surgical indications involving the use of materials with the presently claimed characteristics, including their anti-adhesive properties.

For purely illustrative purposes, reported hereafter are some examples of multilayer nonwoven tissues according to the present invention.

EXAMPLE 1

A multilayer nonwoven tissue composed of a layer of hyaluronic acid benzyl ester, HYAFF 11, and a layer of nonwoven viscose (Jettex 2005 for ORSA), basis weight 80 g/mq, thickness 2 mm, and water absorption percentage 560% by weight, was obtained by the following procedure.

The layer which comes into contact with the skin comprises fibers of HYAFF 11 produced by the wet-spinning technique in the form of a 30 g/mq sheet. Fibers were made into sheets as described in WO 93/11803.

This layer is joined by stitching to a second layer of nonwoven viscose tissue with a basis weight of 30 g/mq.

The final nonwoven product thus comprises two perfectly adhered layers with a total basis weight of 80 g/mq, a thickness of 2 mm, and a water absorption percentage of 560% by weight.

EXAMPLE 2

A multilayer nonwoven tissue comprising a layer of hyaluronic acid ethyl ester, HYAFF 7, and a layer of nonwoven polyester (BEST BOND 20 PS from FNT), with a basis weight of 50 g/mq, a thickness of 1 mm, and a water absorption of 400% by weight, is obtained according to the following procedure.

The layer which comes into contact with the skin comprises fibers of HYAFF 7 produced by the wet-spinning technique in a 30-g/mq sheet which is joined by stitching to a second layer of nonwoven polyester with a basis weight of 20 g/mq.

The final nonwoven product is thus composed of two perfectly adhered layers with a total basis weight of 50 g/mq, a thickness of 1 mm, and a water absorption percentage of 400% by weight.

EXAMPLE 3

A multilayer nonwoven tissue comprising a mixed layer of hyaluronic acid benzyl ester, HYAFF 11, and calcium alginate in a 1:1 ratio and a reinforcing nonwoven tissue of polypropylene (spunbonded nonwoven base, 50 g/mq from NEUBERGER) with a basis weight of 70 g/mq, a thickness of 1.5 mm, and a water absorption percentage of 450% by weight, was obtained by the following procedure.

Fibers of HYAFF 11 and calcium alginate, 40 mm in length, obtained by conventional wet-spinning techniques, were mixed, made into a 20 g/mq sheet, and joined by stitching to a spunbonded nonwoven tissue with a basis weight of 50 g/mq.

The resulting material comprises two layers of nonwoven tissue with a total basis weight of 70 g/mq, a thickness of 1.5 mm, and a water absorption percentage of 450% by weight.

EXAMPLE 4

A multilayer nonwoven tissue comprising a layer of the 75% partial benzyl ester of hyaluronic acid, HYAFF 11p75, and a layer of polyurethane foam such as LYOBEND (from DELCON) with a basis weight of 100 g/mq, a thickness of 5 mm, and a water absorption percentage of 950% by weight, was obtained by the following procedure.

The layer which comes into contact with the skin comprises fibers of HYAFF 11p75 produced by the wet-spinning technique made into a 45 g/mq sheet and joined by stitching to a second layer of polyurethane foam.

The resulting nonwoven product comprises two layers perfectly joined together, with a total basis weight of 100 g/mq, a thickness of 4 mm, and a water absorption percentage of 950% by weight.

EXAMPLE 5

A multilayer nonwoven tissue comprising a layer of hyaluronic acid benzyl ester HYAFF 11 and a layer of polyurethane foam such as LYOBEND (from DELCON) with a basis weight of 100 g/mq, a thickness of 6 mm, and a water absorption percentage of 860% by weight, was obtained by the following procedure.

The layer which comes into contact with the skin comprises fibers of HYAFF 11 produced by the wet-spinning technique and made into a 45 g/mq sheet which is joined by stitching to a second layer of polyurethane foam.

The resulting nonwoven product comprises two perfectly adhered layers with a total basis weight of 100 g/mq, a thickness of 6 mm, and a water absorption percentage of 860% by weight.

EXAMPLE 6

A multilayer nonwoven tissue comprising three layers, with a basis weight of 200 g/mq and a thickness of 3 mm, wherein the layer coming into contact with the skin comprises a mixture of the partial benzyl ester of hyaluronic acid, HYAFF 11p75, and the benzyl ester of alginic acid, ALAFF 11, in equal proportions, a second layer comprising a cushion of polyurethane foam such as DS 50 FOAM (from ORSA) with a density of 55/69 Kg/cc (UNI regulation 6349), and a third layer comprising a polyurethane membrane with a water vapour permeability of 426 g/mq in 24 hours, was obtained according to the following procedure. The preparation of ALAFF 11 and other total and partial esters of alginic acid is described in EPA 0 251 905 and U.S. Pat. No. 5,264,422.

Fibers of HYAFF 11 and ALAFF 11, 40 mm in length, obtained by a wet-spinning process, were stitched to the surface of the polyurethane foam cushion while the other surface was adhered with DURO-TAK 380-1054 glue (from NATIONAL) to the polyurethane membrane. The final material comprises three layers with a final basis weight of 200 g/mq, a thickness of 8 mm, a water absorption percentage of 1100% by weight, and a vapour permeability value of 450 g/mq in 24 hours.

EXAMPLE 7

A multilayer nonwoven tissue comprising a layer of hyaluronic acid benzyl ester, HYAFF 11, and a layer of nonwoven viscose (Jettex 2005 from ORSA) with a basis weight of 80 g/mq and a thickness of 2 mm, joined to a HYAFF 11 membrane perforated with 0.5 mm holes produced as described in European Patent Application No. 0 462 426, was obtained according to the following procedure.

The HYAFF 11 surface of a nonwoven tissue obtained as described in Example 1 is sprayed with a solution of HYAFF 11/DMSO at a concentration of 60 mg/ml, after which a perforated membrane with 0.5 mm holes is applied to it. The membrane and nonwoven tissue are then pressed together, immersed in an ethanol bath, washed, and dried.

The nonwoven tissue thus obtained has a basis weight of 80 g/mq, a thickness of 2 mm, and comprises three layers, one of which is formed by a perforated membrane with 0.5 mm holes.

The invention being thus described, it is clear that the same can be modified in various ways. Such modifications are not to be considered as divergences from the spirit and purposes of the present invention, and any modification which would appear evident to an expert in the art comes within the scope of the following claims.

We claim:

1. A multilayer nonwoven material, comprising a surface layer which comes into contact with the skin, and one or more other layers which do not come into contact with the skin, wherein said surface layer which comes into contact with the skin is a member selected from the group consisting of a surface layer comprising at least one hyaluronic acid ester, a surface layer comprising a mixture of said at least one hyaluronic acid ester and at least one natural polymer, semisynthetic polymer, or synthetic polymer, and a surface layer comprising a natural, synthetic, or semisynthetic biocompatible perforated membrane compatible with cell growth on its surface.

2. A multilayer nonwoven material according to claim 1, wherein said at least one natural polymer is a member selected from the group consisting of collagen, a collagen-glycosaminoglycan coprecipitate, cellulose, chitin, chitosan, pectin, pectic acid, agar, agarose, xanthan gum, gellan, alginic acid, an alginate, a polymannan, a polyglycan, a starch, and a natural gum; said at least one semisynthetic polymer is a member selected from the group consisting of an alginic acid ester, cross-linked collagen, a cellulose derivative, an alginic acid derivative, a starch derivative, a hyaluronic acid derivative, a chitin derivative, a chitosan derivative, a gellan derivative, a xanthan derivative, a pectin derivative, a pectic acid derivative, a polyglycan derivative, a polymannan derivative, an agar derivative, an agarose derivative, a derivative of a natural gum, and a glycosaminoglycan derivative; and said at least one synthetic polymer is a member selected from the group consisting of polylactic acid, polyglycolic acid, a copolymer of polylactic acid and polyglycolic acid, a copolymer of a derivative of polylactic acid and a derivative of polyglycolic acid, a polydioxane, a polyphosphazene, a polysulfone, and a polyurethane.

3. A multilayer nonwoven material according to claim 1, wherein said one or more other layers which do not come into contact with the skin comprise a natural, synthetic, or semisynthetic material which acts as a reinforcement and/or a fluid absorption system for said multilayer nonwoven material.

4. A multilayer nonwoven material according to claim 3, wherein said natural material is cotton, said synthetic material is a member selected from the group consisting of viscose rayon, a polyester, a polyamide, a polyalkylene, a mixture of any of the foregoing, a polyurethane, elastomeric silicone, and elastomeric polyurethane, and said semisynthetic material is at least one hyaluronic acid ester.

5. A multilayer nonwoven material according to claim 1, wherein said at least one hyaluronic acid ester is a member selected from the group consisting of a benzyl ester of hyaluronic acid and an ethyl ester of hyaluronic acid.

6. A multilayer nonwoven material according to claim 5, wherein said benzyl ester of hyaluronic acid is a 75% partial benzyl ester of hyaluronic acid.

7. A multilayer nonwoven material according to claim 1, wherein said surface layer which comes into contact with the skin comprises a mixture of a hyaluronic acid benzyl ester and an alginic acid benzyl ester.

8. A multilayer nonwoven material according to claim 1, wherein said surface layer which comes into contact with the skin comprises a mixture of a hyaluronic acid benzyl ester and calcium alginate.

9. A multilayer nonwoven material according to claim 1, wherein said surface layer which comes into contact with the skin comprises a natural, synthetic or semisynthetic biocompatible perforated membrane which is compatible with cell growth on its surface.

10. A multilayer nonwoven material according to claim 11, wherein said natural, synthetic, or semisynthetic biocompatible perforated membrane has a thickness of between 10 and 500μ and possesses a regular series of holes with a definite and constant calibre of between 10 and 1000μ, wherein each hole is separated from its neighbor by a distance of between 50 and 1000μ.

11. A multilayer nonwoven material according to claim 9, wherein said semisynthetic biocompatible perforated membrane comprises at least one hyaluronic acid ester.

12. A multilayer nonwoven material according to claim 11, wherein said at least one hyaluronic acid ester is a hyaluronic acid benzyl ester.

13. A multilayer nonwoven material according to claim 9, wherein said natural biocompatible perforated membrane comprises a material selected from the group consisting of collagen, a coprecipitate of collagen and a glycosaminoglycan, cellulose, chitin, chitosan, a pectin, a pectic acid, agar, agarose, xanthan gum, gellan, alginic acid, an alginate, a polymannan, a polyglucan, a starch, a natural rubber, a mixture of any of the foregoing, a mixture of any of the foregoing with a synthetic polymer, and a mixture of any of the foregoing with a semisynthetic polymer.

14. A multilayer nonwoven material according to claim 9, wherein said synthetic biocompatible perforated membrane comprises a material selected from the group consisting of polylactic acid, polyglycolic acid, a copolymer of polylactic acid and polyglycolic acid, a copolymer of a derivative of polylactic acid and a derivative of polyglycolic acid, a polydioxanone, a polyphosphazene, a polysulfone, a polyurethane, a semisynthetic derivative of a natural polymer, a cellulose derivative, alginic acid, starch, chitin, chitosan, gellan, xanthan gum, a pectin, a pectic acid, a polyglucan, a polymannan, agar, agarose, a natural rubber, a glycosaminoglycan, silicone, silane, a siloxane rubber, a fluoropolymer, polystyrene, vinyl polychloride, polyacrylate, a derivative of polyacrylate, polyhydroxyacrylate, polyhydroxymethacrylate, a carboxyvinyl polymer, a carboxyvinyl polymer derivative, a maleic anhydride polymer, a maleic anhydride polymer derivative, polyvinylchloride, polyvinylalcohol, a polyvinylalcohol derivative, polyethylene, and polypropylene.

15. A multilayer nonwoven material according to claim 14, wherein said semisynthetic derivative of a natural polymer is collagen crosslinked with a crosslinking agent selected from the group consisting of a dialdehyde, a dialdehyde precursor, a dicarboxylic acid, a halide of a dicarboxylic acid, and a diamine.

16. A multilayer nonwoven material according to claim 14, wherein said fluoropolymer is a material selected from the group consisting of polyfluoroethylene, polyfluoropropylene, and a polyfluoroether.

17. A multilayer nonwoven material according to claim 1, wherein said one or more other layers which do not come in contact with the skin are selected from the group consisting of viscose, nonwoven spunbonded polypropylene and polyurethane foam.

18. A multilayer nonwoven material according to claim 1, having a basis weight of between 40 g/mq and 500 g/mq, a thickness of between 0.5 mm and 20 mm, a fiber diameter of between 8 μm and 60 μm, a length of between 5 mm and 100 mm, 2 to 4 layers, a water absorption percentage of 60 % to 500% , and a water vapour permeability value of between 100 and 4500 g/mq in 24 hours.

19. A multilayer nonwoven material according to claim 1, wherein said surface layer which comes into contact with the skin and said one or more other layers which do not come into contact with the skin are fixed together by at least one member selected from the group consisting of a coagulating chemical agent, an adhesive agent, and mechanical stitches.

20. A multilayer nonwoven material according to claim 1, comprising two or more layers stitched together.

21. A multilayer nonwoven material according to claim 1, comprising two layers stitched together, wherein said layer which does not come into contact with the skin comprises a polyurethane foam.

22. A multilayer nonwoven material according to claim 1, comprising three layers, wherein said layer which comes into contact with the skin is a biocompatible perforated membrane comprising a total benzyl ester of hyaluronic acid.

23. A multilayer nonwoven material according to claim 1, containing a pharmaceutically active compound.

24. A multilayer nonwoven material according to claim 23, wherein said pharmaceutically active compound is a member selected from the group consisting of an antibiotic, an antiseptic, an antimitotic, a polypeptide, and a protein.

25. A method of covering or treating a body area of a patient in need therof during a medical procedure comprising covering said body area with a multilayer nonwoven material of any one of claims 1, 3, 19 or 23.

26. A method of claim 25 wherein said medical procedure is selected from the group consisting of surgery, treatment of skin pathologies, dermatology, odontostomatology, orthopaedics, neurosurgery and treatment of an ear or nose.

* * * * *